(12) United States Patent
Castro

(10) Patent No.: US 10,085,769 B2
(45) Date of Patent: Oct. 2, 2018

(54) DILATING CANNULA WITH RADIALLY EXPANDABLE FLANGE

(71) Applicant: TELEFLEX MEDICAL INCORPORATED, Research Triangle Park, NC (US)

(72) Inventor: Salvatore Castro, Raleigh, NC (US)

(73) Assignee: TELEFLEX MEDICAL INCORPORATED, Morrisville, NC (US)

(*) Notice: Subject to any disclaimer, the term of this patent is extended or adjusted under 35 U.S.C. 154(b) by 0 days.

(21) Appl. No.: 14/207,987

(22) Filed: Mar. 13, 2014

(65) Prior Publication Data

US 2014/0276584 A1 Sep. 18, 2014

Related U.S. Application Data

(60) Provisional application No. 61/785,383, filed on Mar. 14, 2013.

(51) Int. Cl.
*A61B 17/34* (2006.01)
*A61M 25/00* (2006.01)

(52) U.S. Cl.
CPC ...... *A61B 17/3439* (2013.01); *A61B 17/3431* (2013.01); *A61M 2025/0024* (2013.01)

(58) Field of Classification Search
CPC . A61B 17/3417; A61B 17/3439; A61B 17/34; A61B 17/3421; A61B 17/02; A61B 17/0206; A61B 17/0293; A61B 2017/0237; A61B 1/00154; A61B 1/32; A61M 25/0668; A61M 25/0102

USPC ......... 604/164.11, 164.01, 164.03, 160, 525, 604/506, 264, 104; 600/224, 229, 201, 600/219, 222

See application file for complete search history.

(56) References Cited

U.S. PATENT DOCUMENTS 668,879 A * 2/1901 Miller .................. A01N 1/00
27/21.1
3,703,898 A * 11/1972 Zackheim ............... A61D 1/02
604/105

(Continued)

FOREIGN PATENT DOCUMENTS

JP H08266549 A 10/1996
JP H09108232 A 4/1997

(Continued)

*Primary Examiner* — Christopher L Templeton
(74) *Attorney, Agent, or Firm* — Baker Hostetler LLP

(57) ABSTRACT

A dilating cannula includes a radially expandable flange and an expandable shaft. The radially expandable flange is disposed at a proximal end portion of the dilating cannula and includes two or more sectors that are each independently movable. The expandable shaft extends from the proximal end portion to a distal end portion of the dilating cannula and defines an inner passageway of the dilating cannula and includes two or more arms. A first branch of the two or more arms extends from one end of the base section and a second branch of the two or more arms extends from another end of the base section. The first branch is connected to a first sector of the two or more sectors of the radially expandable flange and the second branch is connected to a second, different sector of the two or more sectors of the radially expandable flange.

18 Claims, 2 Drawing Sheets

(56) References Cited

U.S. PATENT DOCUMENTS

| | | | |
|---|---|---|---|
| 4,865,593 A * | 9/1989 | Ogawa | A61M 25/0668 604/160 |
| 4,921,479 A * | 5/1990 | Grayzel | A61M 25/0668 604/160 |
| 5,609,604 A | 3/1997 | Schwemberger et al. | |
| 5,814,073 A * | 9/1998 | Bonutti | A61B 17/0401 604/14 |
| 5,957,902 A | 9/1999 | Teves | |
| 7,195,592 B2 | 3/2007 | Ravikumar et al. | |
| 8,206,370 B2 * | 6/2012 | von Oepen | A61M 25/0029 604/164.01 |
| 2005/0159650 A1 * | 7/2005 | Raymond | A61B 17/02 600/201 |
| 2006/0074278 A1 * | 4/2006 | Petit | A61B 17/0293 600/224 |
| 2006/0106416 A1 | 5/2006 | Raymond et al. | |
| 2007/0004968 A1 | 1/2007 | Bonadio et al. | |
| 2007/0156024 A1 * | 7/2007 | Frasier | A61B 17/02 600/219 |
| 2008/0051734 A1 | 2/2008 | Bonutti et al. | |
| 2008/0103366 A1 * | 5/2008 | Banchieri | A61B 1/32 600/208 |
| 2009/0048622 A1 | 2/2009 | Wilson | |
| 2009/0221965 A1 * | 9/2009 | Osypka | A61M 25/0662 604/160 |
| 2009/0306586 A1 * | 12/2009 | Ross | A61B 17/3439 604/93.01 |
| 2011/0009705 A1 | 1/2011 | Bombard et al. | |
| 2012/0172668 A1 * | 7/2012 | Kerns | A61B 17/3439 600/208 |
| 2014/0303666 A1 * | 10/2014 | Heiman | A61B 17/0218 606/198 |

FOREIGN PATENT DOCUMENTS

| | | |
|---|---|---|
| JP | 2007283123 A | 11/2007 |
| JP | 2011251134 A | 12/2011 |
| WO | 2003/001969 A2 | 1/2003 |
| WO | 2004/067062 A2 | 8/2004 |

* cited by examiner

DILATING CANNULA WITH RADIALLY EXPANDABLE FLANGE

CROSS REFERENCE TO RELATED APPLICATION

This application claims the benefit of U.S. Provisional Application No. 61/785,383, filed on Mar. 14, 2013, the disclosure of which is hereby incorporated by reference in its entirety.

TECHNICAL FIELD

This disclosure generally relates to surgical tools. More particularly, this disclosure relates to a dilating cannula with a radially expandable flange that expands an opening formed in a body cavity and a method of using the dilating cannula with the radially expandable flange.

BACKGROUND

Surgery often requires the formation of an opening within a body cavity that is to be operated on. Depending on the size of the opening, the healing of such an opening can require a lengthy recovery time. Moreover, a relatively large opening may leave a permanent scar on the skin, which is undesirable to patients.

To avoid forming relatively large openings in body cavities, minimally invasive surgery, e.g., laparoscopic surgery, is a current surgical technique in which operations are performed through a relatively small opening with diameters of about 0.5 mm to 10 mm. Such minimally invasive surgery provides the benefits of reduced pain and shorter recovery times.

Moreover, it is known that incisions smaller than about 3.0 mm greatly reduce the likelihood of permanent scarring. However, many tools required for surgery have dimensions greater than 3.0 mm and, therefore, cannot enter the body cavity through 3.0 mm openings. Therefore, the benefits of minimal scarring and even shorter recovery times cannot be realized in many surgeries.

Therefore, a need exists for a dilating cannula that is radially expandable both inside and outside of the opening to receive surgical tools that cannot fit within the formed opening without increasing the size of the incision or tearing other tissue in the body cavity.

SUMMARY

The foregoing needs are met, to a great extent, by implementations of the dilating cannula with the radially expandable flange and of the methods for using the dilating cannula with the radially expandable flange.

In accordance with one implementation, a surgical assembly includes a dilating cannula and a needle-tipped obturator. The dilating cannula includes a radially expandable flange including two or more sectors that are each independently movable. The radially expandable flange is disposed at a proximal end portion of the dilating cannula. The dilating cannula also includes an expandable shaft extending from the proximal end portion to a distal end portion of the dilating cannula. The expandable shaft defines an inner passageway of the dilating cannula and includes two or more arms. Each of the two or more arms includes elongate longitudinal strips adjacent to the inner passageway and includes a base section that is disposed at the distal end portion of the dilating cannula. Each of the two or more arms also includes a first branch that extends from one end of the base section and a second branch that extends from another end of the base section. The first branch is connected to a first sector of the two or more sectors of the radially expandable flange and the second branch is connected to a second, different sector of the two or more sectors of the radially expandable flange. The needle-tipped obturator includes a handle including a knob and an annular projection extending from the knob, a shaft connected to the handle, and a needle tip connected to the shaft.

In some implementations, the radially expandable flange can include an annular projection including two or more sectors. The annular projection of the handle can define an annular opening configured to receive the annular projection of the radially expandable flange. The shaft can have a first dimension in an axis perpendicular to a center axis of the needle-tipped obturator and the needle tip can have a second dimension in an axis perpendicular to a center axis of the needle-tipped obturator that is greater than the first dimension of the shaft. The first dimension of the shaft can be substantially equal to a dimension of an inner passageway defined by the expandable shaft in an axis perpendicular to a center axis of the surgical assembly. The needle tip can be configured to form an opening in a body cavity.

In accordance another implementation, a dilating cannula includes a radially expandable flange including two or more sectors that are each independently movable. The radially expandable flange is disposed at a proximal end portion of the dilating cannula. The dilating cannula also includes an expandable shaft extending from the proximal end portion to a distal end portion of the dilating cannula. The expandable shaft defines an inner passageway of the dilating cannula and includes two or more arms. Each of the two or more arms includes elongate longitudinal strips adjacent to the inner passageway and includes a base section. Each base section is disposed at the distal end portion of the dilating cannula. A first branch of the two or more arms extends from one end of the base section, and a second branch of the two or more arms extends from another end of the base section. The first branch is connected to a first sector of the two or more sectors of the radially expandable flange and the second branch is connected to a second, different sector of the two or more sectors of the radially expandable flange.

In some implementations, the radially expandable flange can include an annular projection including two or more sectors. The annular projection can extend axially from a proximal face of the radially expandable flange. The radially expandable flange can define a center hub having a diameter equal to a diameter of the expandable shaft. The annular projection can include the same number of sectors as the radially expandable flange. The radially expandable flange can include four sectors and the expandable shaft can include four arms.

In some implementations, an outer circumferential length of each of the two or more sectors of the radially expandable flange can be equal. The radially expandable flange can be perpendicular to a center axis of the expandable shaft. The two or more arms of the expandable shaft can be flat. The axial dimension of the expandable shaft can be greater than a radial dimension of the radially expandable flange. The first branch and the second branch can define a longitudinal slit and each pair of the two or more sectors of the radially expandable flange can be separated by a sector slit that is aligned along a single plane with the longitudinal slit.

In accordance with another implementation, a dilating cannula includes a radially expandable flange including two or more sectors that are each independently movable. The radially expandable flange is disposed at a proximal end portion of the dilating cannula. The dilating cannula also includes an expandable shaft extending from the proximal end portion to a distal end portion of the dilating cannula. The expandable shaft defines an inner passageway of the dilating cannula and includes two or more arms. Each of the two or more arms includes elongate longitudinal strips adjacent to the inner passageway and includes a base section. Each base section is disposed at the distal end portion of the dilating cannula. A first branch of the two or more arms extends from one end of the base section, and a second branch of the two or more arms extends from another end of the base section. The first branch and the second branch define a longitudinal slit. Each pair of the two or more sectors of the radially expandable flange is separated by a sector slit and the sector slit is aligned along a single plane with the longitudinal slit.

In accordance with still another implementation, a method for inserting a surgical device in an opening formed in a body cavity is disclosed. Initially, an opening in a body cavity is formed by inserting at least part of a surgical assembly in the body cavity. The surgical assembly includes a dilating cannula over a needle-tipped obturator. The dilating cannula includes a radially expandable flange disposed at a proximal end portion of the dilating cannula and an expandable shaft extending from the proximal end portion to a distal end portion of the dilating cannula. The radially expandable flange is located outside of the opening.

The needle-tipped obturator is then removed from the surgical assembly while maintaining at least part of the expandable shaft of the dilating cannula within the opening of the body cavity. Finally, a surgical tool is inserted within the dilating cannula. The surgical tool has a dimension in an axis perpendicular to a center axis of the surgical tool that is greater than a dimension of the expandable shaft of the dilating cannula in the axis perpendicular to the center axis of the surgical assembly. Insertion of the surgical tool causes expansion of both the radially expandable flange and the expandable shaft of the dilating cannula.

In some implementations, removal of the needle-tipped obturator from the surgical assembly can cause expansion of both the radially expandable flange and the expandable shaft of the dilating cannula. The surgical tool can be removed from the dilating cannula, which causes the dilating cannula to automatically return to its unstressed configuration. The needle-tipped obturator can be placed partially within the dilating cannula to assemble the surgical assembly.

Certain implementations of the dilating cannula with the radially expandable flange and the method of using the dilating cannula with the radially expandable flange have been outlined so that the detailed description below may be better understood. There are, of course, additional implementations that will be described below and which will form the subject matter of the claims.

In this respect, before explaining at least one implementation in detail, it is to be understood that the dilating cannula with a radially expandable flange is not limited in its application to the details of construction and to the arrangements of the components set forth in the following description or illustrated in the drawings. Also, it is to be understood that the phraseology and terminology employed herein, as well as in the Abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the dilating cannula with a radially expandable flange. It is understood, therefore, that the claims include such equivalent constructions insofar as they do not depart from the spirit and scope of the present application.

DETAILED DESCRIPTION

Figure 1:
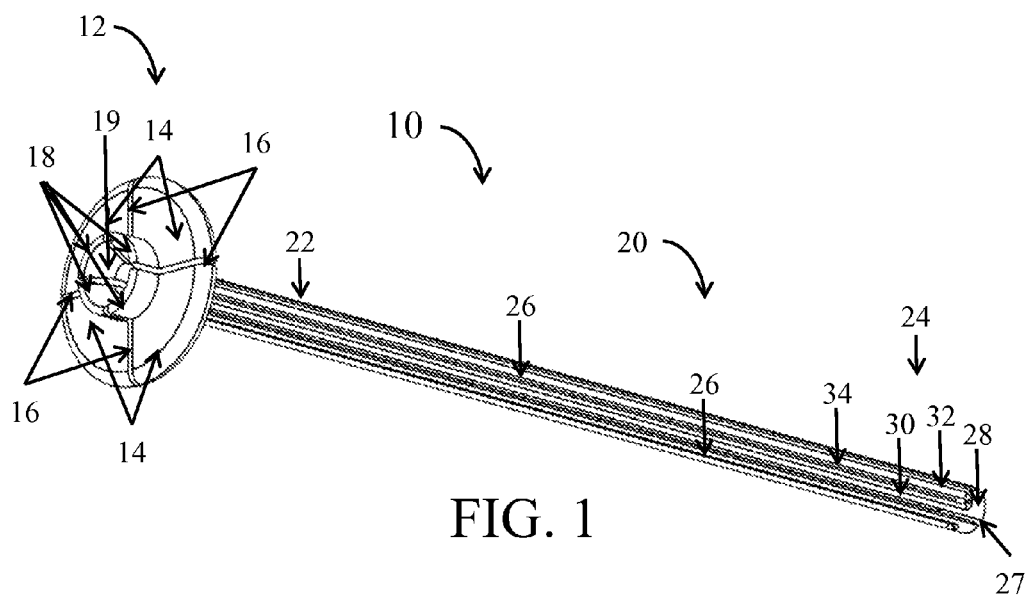
FIG. 1 is a perspective view illustrating an exemplary dilating cannula with a radially expandable flange.

Implementations of the dilating cannula with the radially expandable flange and the method of using the dilating cannula with the radially expandable flange are described with reference to the drawings, in which like reference numerals refer to like parts throughout.

Referring to FIG. 1, a dilating cannula 10 with a radially expandable flange 12 is illustrated. The dilating cannula 10 includes the radially expandable flange 12 being disposed at a proximal end portion of the dilating cannula and an expandable shaft 20 extending from the proximal end portion to a distal end portion of the dilating cannula. The expandable shaft 20 has a proximal end portion 22 opposite a distal end portion 24. In some implementations, as shown in FIG. 1, the radially expandable flange 12 can be circular. In other implementations, the radially expandable flange 12 can be any geometric shape, such as, for example, an oval, a triangle, a square, a pentagon, a hexagon, or the like.

The radially expandable flange 12 includes four sectors 14 that are separated from one another by four slits 16 and, thus, are independently movable. The sectors 14 can extend perpendicularly relative to the center axis of the expandable shaft 20. The radial dimension between the inner wall and outer wall of each sector 14 is less than an axial length of the expandable shaft 20 between the proximal end portion 22 and distal end portion 24. Four annular projections 18 extend axially from a proximal face of the radially expandable flange 12, such that each annular projection 18 is connected to one sector 14. Each annular projection 18 extends circumferentially along an inner wall of a sector 14. The inner and outer circumferential lengths of each projection 18 can be equal. The sectors 14 define a hub 19 that is coaxial with an outer wall of the sectors 14. The central axis of the hub 19, the radially expandable flange 12, and an expandable shaft 20 can be the same. The hub 19 can have a diameter ranging from 0.5 mm to 100 mm and, preferably, have a diameter of about 1.0 mm to 3.0 mm.

In some implementations, as shown in FIG. 1, the radially expandable flange 12 can include four sectors 14. In other implementations, the radially expandable flange 12 can include any number of two or more sectors 14. The radially expandable flange 12 can be, preferably, made from a rigid material, such as, for example, a rigid plastic or a rigid metal. The radially expandable flange 12 may be rigid so that it maintains its structure without deformation if struck by a surgical tool being inserted into the dilating cannula 10.

The expandable shaft 20 includes four arms 26 extending from the proximal end portion 22 to the distal end portion 24 of the expandable shaft 20. Each arm 26 can be U-shaped and include a base section 28 at the distal end portion 24, a first branch 30 extending from one end of the base section 28, and a second branch 32 extending from the other end of the base section 28. In some implementations, as shown in FIG. 1, the base section 28 can be curved, while in other implementations, the base section 28 can be flat.

A slit 34 is defined between the first branch 30 and the second branch 32 for each arm 26. The four arms 26 define an inner passageway 27 having a diameter equal that can be equal to the diameter of the hub 19. The diameter of the inner passageway 27 can be, for example, 1.0 to 3.0 mm. In some implementations, as shown in FIG. 1, the expandable shaft 20 includes four arms 26. In other implementations, the expandable shaft 20 can include any number of two or more arms 26. Preferably, however, the number of arms 26 can be equal to the number of sectors 14.

The proximal end portion 22 of the first branch 30 is connected to one sector 14 and the proximal end of the second branch 32 is connected to another sector 14. The proximal ends 22 of the first branch and the second branch 32 are connected to a distal face of the each sector 14, adjacent to the inner wall of the sectors 14. As shown in FIG. 1, each slit 34 is aligned with a corresponding slit 16 along the same plane. In some implementations, as shown in FIG. 1, the arms 26 can be formed from a strip, such that the base section 28, first branch 30, and the second branch 32 are flat. In other implementations, the arms 26 can be formed from, for example, a wire, such that the base section 28, first branch 30, and the second branch 32 are round.

Because each sector 14 of the radially expandable flange 12 is connected to two different arms 26, the dilating cannula 10 maintains it structure and does not disassemble or separate, even though the sectors 14 and the arms 26 are individually separate. The arms can be, preferably, made from a resilient material that allows the first branch 30 and the second branch 32 to flex as the radially expandable flange 12 expands and then return to their unstressed configuration. The resilient material can be, for example, resilient plastic, resilient rubber, resilient carbon fiber, resilient metal, resilient metal alloy, or the like.

Figure 2:
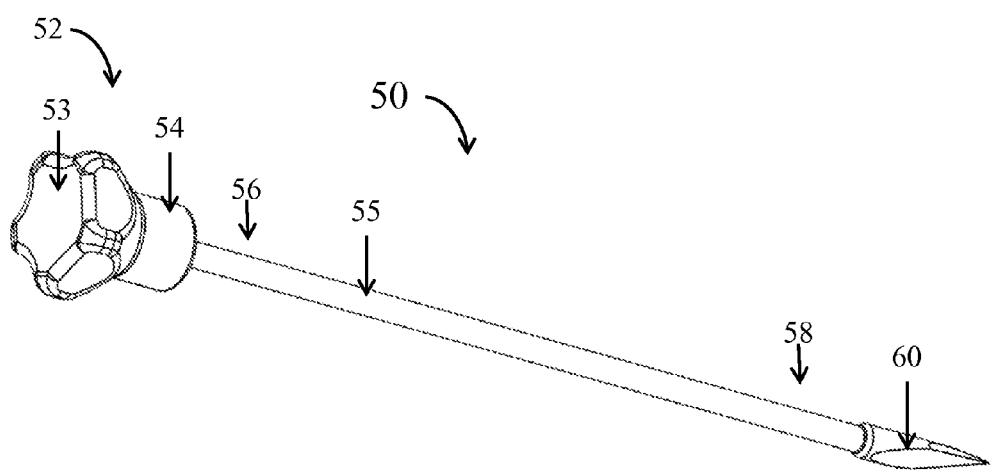
FIG. 2 is a perspective view illustrating an exemplary needle-tipped obturator.

Referring to FIG. 2, a needle-tipped obturator 50 is illustrated. The needle-tipped obturator 50 includes a handle 52 including a knob 53 and an annular projection 54, a shaft 55 having a proximal end 56 and a distal end 58, and a needle tip 60. The handle 52 is connected to the proximal end 56 of the shaft 55 and the needle tip 60 is connected to the distal end 58 of the shaft 55. The annular projection 54 extends in a distal direction from the knob 53.

In some implementations, as shown in FIG. 2, the knob 53 has a generally pentagonal shape to enable allow a medical practitioner to effectively grip and maneuver the needle-tipped obturator 50. In other implementations, the knob 53 can have any geometric shape, such as, for example, an oval, a triangle, a square, a pentagon, a hexagon, or the like. The handle 52 can be, preferably, made from a rigid material, such as, for example, a rigid plastic or a rigid metal.

The shaft 55 can have a generally tubular shape, as shown in FIG. 2. However, in some implementations, the shaft 55 can have any geometric shape capable of being received within the inner passageway 27. For example, a cross section of the shaft 55 perpendicular to its center axis can be any geometric shape, such as, for example, an oval, a triangle, a square, a pentagon, a hexagon, or the like. The diameter of the shaft 55 can be, preferably, equal to the diameter of the inner passageway 27. As such, the diameter of the shaft 55 can be, for example, 1.0 mm to 3.0 mm.

The needle tip 60 is configured to form an opening in a body cavity. At its proximal end, the needle tip 60 can have an enlarged head with a diameter that is greater than the diameter of the shaft 55. As such, the largest diameter of the needle tip 60 can be greater than the diameter of the hub 19 or the inner passageway 27 of the dilating cannula 10. Therefore, when the needle-tipped obturator 50 is inserted into the dilating cannula 10, the needle tip 60 causes the radially expandable flange 12 and expandable shaft 20 to expand, thereby increasing the diameter of the hub 19 and allowing the needle tip 60 to pass through the radially expandable flange 12 and expandable shaft 20.

Figure 3:
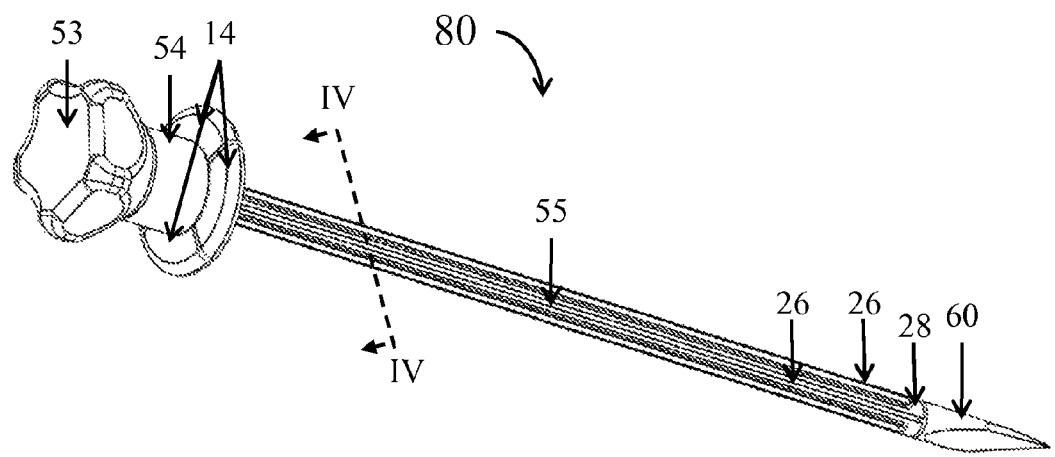
FIG. 3 is a perspective view illustrating an exemplary surgical assembly including the needle-tipped obturator inserted within the dilating cannula with the radially expandable flange.

Referring to FIG. 3, a surgical assembly 80 including the needle-tipped obturator 50 inserted into the dilating cannula 10 is illustrated. The needle-tipped obturator 50 and the dilating cannula 10 are connected to one another using a friction fit, as described in greater detail below. The surgical assembly 80 is configured to be inserted in a body cavity to form an opening for surgery. Following removal of the needle-tipped obturator 50, the opening in the body cavity will be defined by the dilating cannula 10.

Figure 4:
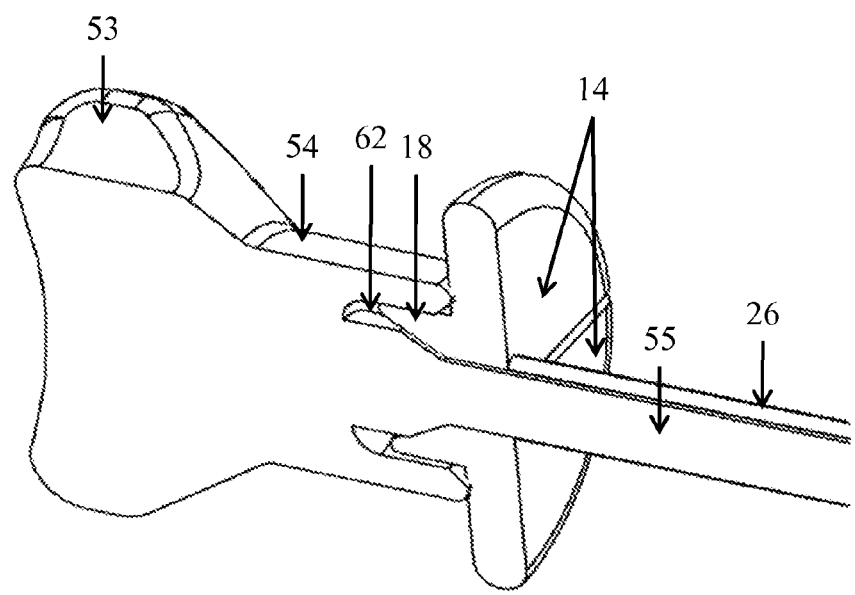
FIG. 4 is a larger-scale perspective cross-section of the surgical assembly along the line IV-IV.

Referring to FIG. 4, a cross-section of a proximal end of the surgical assembly 80 taken along line IV-IV is illustrated. The annular projection 54 of the handle 52 defines an annular opening 62 configured to receive and hold the annular projection 18 of the radially expandable flange 12 through a friction fit when the needle-tipped obturator 50 is inserted into the dilating cannula 10. The annular projection 54 can have a thickness that allows the annular projection 54 to slightly flex to receive and hold the annular projection 18. The friction fit between the annular projection 54 and the annular projection 18 should have sufficient strength so that the needle-tipped obturator 50 and the dilating cannula 10 do not separate while the medical practitioner is forming an opening in a body cavity.

A surgical device can be inserted in the opening of the body cavity using the dilating cannula 10. In particular, a surgical device having a diameter greater than the diameter of the hub 19 in an unstressed configuration can be inserted in the opening of the body cavity without increasing the size of the incision or tearing other tissue in the body cavity. As such, a greater variety of surgical tools with, for example, larger heads can be used to perform surgery, while maintaining the incision size of, for example, 1.0 mm to 3.0 mm to reduce the likelihood of permanent scarring.

First, the opening can be formed in the body cavity by inserting at least part of the surgical assembly 80 in the body cavity. The needle tip 60 tears tissue in the body cavity to form the opening in the body cavity. The radially expandable flange 12 is located outside of the formed opening.

Next, the needle-tipped obturator 50 is removed from the surgical assembly 80 while at least part of the expandable shaft 20 of the dilating cannula 10 is maintained within the body cavity to define the opening. Because the needle tip 60 of the needle-tipped obturator 50 has a diameter larger than the diameter of the inner passageway 27 defined by the arms 26 and larger than the diameter of the hub 19, the expandable shaft 20 and, subsequently, the radially expandable flange 12 expand as the needle tip 60 is withdrawn from the dilating cannula 10.

To perform surgery on the body cavity, one or more surgical devices are inserted into the opening of the body cavity through the radially expandable flange 12 and the expandable shaft 20. One or more of the surgical devices may have a diameter that is greater than the diameter of the hub 19 and the inner passageway 27, which causes the radially expandable flange 12 and, subsequently, the expandable shaft 20 to expand as the surgical tool moves axially along the dilating cannula 10 into the opening of the body cavity.

At least part of the dilating cannula 10 can remain in a stressed, expanded configuration while the surgical device is within the dilating cannula. However, once the surgical device is removed from the dilating cannula 10, the dilating cannula can automatically return to its unstressed configuration due to the resilient material of the arms 26.

The many features and advantages of the dilating cannula 10 including the radially expandable flange 12 are apparent from the detailed specification, and thus, the claims cover all such features and advantages within the scope of this application. Further, numerous modifications and variations are possible. As such, it is not desired to limit the dilating cannula 10 to the exact construction and operation described and illustrated, and accordingly, all suitable modifications and equivalents may fall within the scope of the claims.

What is claimed is:

1. A surgical assembly, comprising:
    a dilating cannula, comprising:
        a radially expandable flange comprising two or more sectors, each of the two or more sectors being individually spaced apart and independently movable from each other, the radially expandable flange being disposed at a proximal end portion of the dilating cannula; and
        an expandable shaft extending from the proximal end portion to a distal end portion of the dilating cannula, the expandable shaft defining an inner passageway of the dilating cannula and comprising two or more arms configured to allow a needle tip with a diameter greater than a diameter of the expandable shaft to pass through the expandable shaft, each of the two or more arms comprising a base section and the base sections are separated and movable relative to one another, a first branch extending from one end of the base section, and a second branch extending from another end of the base section, each base section of the two or more arms being disposed at the distal end portion of the dilating cannula, wherein:
            each pair of adjacent sectors of the two or more sectors defines a sector slit therebetween,
            the first branch of a first arm of the two or more arms is connected to a first sector of the two or more sectors of the radially expandable flange,
            the second branch of the first arm of the two or more arms is connected to a second sector of the two or more sectors of the radially expandable flange, different from the first sector of the two or more sectors of the radially expandable flange,
            each of the two or more sectors include a projection, and each of the projections extend circumferentially along an inner wall of a respective sector of the two or more sectors, and
            the radially expandable flange defines a center hub having a diameter equal to a diameter of the expandable shaft; and
    a needle-tipped obturator, comprising:
        a handle comprising a knob and an annular projection extending from the knob;
        a shaft connected to the handle; and
        a needle tip connected to the shaft.

2. The surgical assembly of claim 1, wherein the annular projection of the handle defining an annular opening is configured to receive the projections of the two or more sectors of the radially expandable flange.

3. The surgical assembly of claim 1, wherein:
    the shaft has a first dimension in an axis perpendicular to the center axis of the needle-tipped obturator, and
    the needle tip has a second dimension in an axis perpendicular to the center axis of the needle-tipped obturator that is greater than the first dimension of the shaft.

4. The surgical assembly of claim 1, wherein a first dimension of the shaft is substantially equal to a dimension of the inner passageway defined by the expandable shaft in an axis perpendicular to a center axis of the surgical assembly.

5. The surgical assembly of claim 1, wherein the needle tip is configured to form an opening in a body cavity.

6. A dilating cannula, comprising:
    a radially expandable flange comprising two or more sectors, each of the two or more sectors being individually spaced apart and independently movable from each other, the radially expandable flange being disposed at a proximal end portion of the dilating cannula; and
    an expandable shaft extending from the proximal end portion to a distal end portion of the dilating cannula, the expandable shaft defining an inner passageway of the dilating cannula and comprising two or more arms configured to allow a needle tip with a diameter greater than a diameter of the expandable shaft to pass through the expandable shaft, each of the two or more arms comprising a base section and the base sections are separated and movable relative to one another, a first branch extending from one end of the base section, and a second branch extending from another end of the base section, each base section of the two or more arms being disposed at the distal end portion of the dilating cannula,
    wherein each pair of adjacent sectors of the two or more sectors define a sector slit therebetween,
    wherein the first branch of a first arm of the two or more arms is connected to a first sector of the two or more sectors of the radially expandable flange, and
    wherein the second branch of the first arm of the two or more arms is connected to a second sector of the two or more sectors of the radially expandable flange, different from the first sector of the two or more sectors of the radially expandable flange,
    wherein each of the two or more sectors include a projection, and each of the projections extend circumferentially along an inner wall of a respective sector of the two or more sectors, and
    wherein the radially expandable flange defines a center hub having a diameter equal to a diameter of the expandable shaft.

7. The dilating cannula of claim 6, wherein each of the projections extend axially from a proximal face of the respective sector of the two or more sectors of the radially expandable flange.

8. The dilating cannula of claim 6, wherein the radially expandable flange comprises four sectors and the expandable shaft comprises four arms.

9. The dilating cannula of claim 6, wherein an outer circumferential length of each of the two or more sectors of the radially expandable flange is equal.

10. The dilating cannula of claim 6, wherein the radially expandable flange is perpendicular to a center axis of the expandable shaft.

11. The dilating cannula of claim 6, wherein the two or more arms of the expandable shaft are flat.

12. The dilating cannula of claim 6, wherein an axial dimension of the expandable shaft is greater than a radial dimension of the radially expandable flange.

13. The dilating cannula of claim 6, wherein:
the first branch and the second branch define a longitudinal slit, and
at least one of the sector slits is aligned along a single plane with the longitudinal slit.

14. The dilating cannula of claim 6, wherein the first sector and the second sector are connected via only the arms of the two or more arms.

15. The dilating cannula of claim 6, wherein the first branch of a second arm of the two or more arms is connected to the second sector of the two or more sectors of the radially expandable flange, and
wherein the second branch of the second arm of the two or more arms is connected to a third sector of the two or more sectors of the radially expandable flange, different from the first and second sectors of the two or more sectors of the radially expandable flange.

16. The dilating cannula of claim 6, wherein at least one arm of the two or more arms including the base section, the first branch, and the second branch define a U-shape.

17. The dilating cannula of claim 16, wherein the base section, the first branch, and the second branch of the at least one arm of the two or more arms are flat.

18. A dilating cannula, comprising:
a radially expandable flange comprising two or more sectors, each of the two or more sectors being individually spaced apart and independently movable from each other, the radially expandable flange being disposed at a proximal end portion of the dilating cannula; and
an expandable shaft extending from the proximal end portion to a distal end portion of the dilating cannula, the expandable shaft defining an inner passageway of the dilating cannula and comprising two or more arms configured to allow a needle tip with a diameter greater than a diameter of the expandable shaft to pass through the expandable shaft, each of the two or more arms comprising a base section, a first branch extending from one end of the base section, and a second branch extending from another end of the base section, each base section of the two or more arms being disposed at the distal end portion of the dilating cannula, wherein each pair of adjacent sectors of the two or more sectors define a sector slit therebetween,
wherein the first branch of a first arm of the two or more arms is connected to a first sector of the two or more sectors of the radially expandable flange,
wherein the second branch of the first arm of the two or more arms is connected to a second sector of the two or more sectors of the radially expandable flange, different from the first sector of the two or more sectors of the radially expandable flange,
wherein each of the two or more sectors include a projection, and each of the projections extend circumferentially along an inner wall of a respective sector of the two or more sectors, and
wherein each of the projections extend axially from a proximal face of the respective sector of the two or more sectors of the radially expandable flange.

* * * * *